(12) United States Patent
Magnusson et al.

(10) Patent No.: US 10,667,952 B2
(45) Date of Patent: Jun. 2, 2020

(54) WELDING HELMET HAVING A FILTER ARRANGEMENT

(75) Inventors: Kristina Magnusson, Djurmo (SE); Kenneth Jarefors, Borlange (SE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 834 days.

(21) Appl. No.: 13/989,123

(22) PCT Filed: Nov. 28, 2011

(86) PCT No.: PCT/US2011/062182
§ 371 (c)(1),
(2), (4) Date: Sep. 19, 2013

(87) PCT Pub. No.: WO2012/074895
PCT Pub. Date: Jun. 7, 2012

(65) Prior Publication Data
US 2014/0013479 A1     Jan. 16, 2014

Related U.S. Application Data

(60) Provisional application No. 61/418,524, filed on Dec. 1, 2010.

(51) Int. Cl.
*A61F 9/06*     (2006.01)

(52) U.S. Cl.
CPC .............. *A61F 9/067* (2013.01); *A61F 9/064* (2013.01); *G02F 2201/44* (2013.01)

(58) Field of Classification Search
CPC .. A61F 9/067; A61F 9/06; A61F 9/061; A61F 9/062; A61F 9/064; A61F 9/065; G02F 2201/44; A41D 2600/202; A42B 3/225

USPC ............................................................ 2/427
See application file for complete search history.

(56) References Cited

U.S. PATENT DOCUMENTS

| 2,363,461 | A | * | 11/1944 | Huntsman | ................ | A61F 9/06 |
| | | | | | | 2/12 |
| 2,406,092 | A | * | 8/1946 | Meyer | ...................... | A61F 9/06 |
| | | | | | | 2/8.1 |
| 2,419,649 | A | * | 4/1947 | Lieg | ......................... | A61F 9/06 |
| | | | | | | 2/8.3 |
| 2,719,972 | A | * | 10/1955 | Kelly | ..................... | A61F 9/061 |
| | | | | | | 2/8.3 |

(Continued)

FOREIGN PATENT DOCUMENTS

| CH | 694318 | 11/2004 |
| CN | 201328929 | 10/2009 |

(Continued)

OTHER PUBLICATIONS

International Search Report for PCT International Application No. PCT/US2011/062182, dated Nov. 23, 2012, 5 pages.

*Primary Examiner* — Alissa L Hoey
(74) *Attorney, Agent, or Firm* — Gregg H. Rosenblatt (57) ABSTRACT

A welding helmet (100, 200, 300, 400, 500) having a filter arrangement is disclosed. The welding helmet is provided with a main filter (102, 202, 302, 402, 502) and at least one auxiliary filter (104, 204, 304, 404, 504) separate from and positioned next to the main filter. The at least one auxiliary filter comprises an electro-optic element (10, 20) adapted to attenuate the transmission of optical radiation incident on the auxiliary filter.

13 Claims, 8 Drawing Sheets

(56) References Cited

U.S. PATENT DOCUMENTS

| | | | | |
|---|---|---|---|---|
| 2,762,049 A * | 9/1956 | Herrick | A61F 9/061 | 2/8.3 |
| 2,817,087 A * | 12/1957 | Rush | A61F 9/06 | 2/8.1 |
| 3,239,844 A * | 3/1966 | Hoover | A61F 9/061 | 2/8.3 |
| 3,332,087 A * | 7/1967 | Manz | A61F 9/061 | 2/8.3 |
| 3,339,207 A * | 9/1967 | Perry | A61F 9/061 | 2/8.3 |
| 3,914,027 A * | 10/1975 | Caron | A61F 9/067 | 359/228 |
| 4,039,254 A * | 8/1977 | Harsch | A61F 9/062 | 2/8.4 |
| RE29,684 E * | 6/1978 | Gordon | A61F 9/067 | 2/8.8 |
| 4,155,122 A | 5/1979 | Budmiger | | |
| 4,523,808 A | 6/1985 | Miller | | |
| 4,646,363 A * | 3/1987 | Wood | A61F 9/064 | 2/427 |
| 4,863,244 A * | 9/1989 | Fuerthbauer | A61F 9/067 | 2/431 |
| 4,888,825 A | 12/1989 | Hakala | | |
| 4,953,231 A | 9/1990 | Burnett | | |
| 5,140,707 A * | 8/1992 | Johnson | A61F 9/06 | 2/8.1 |
| 5,191,468 A | 3/1993 | Mases | | |
| 5,224,219 A * | 7/1993 | Edwards | A61F 9/061 | 2/8.3 |
| 5,302,815 A * | 4/1994 | Eggenschwiler | A61F 9/067 | 2/8.8 |
| 5,351,151 A * | 9/1994 | Levy | G02B 3/0043 | 359/237 |
| 5,519,522 A * | 5/1996 | Fergason | B23K 9/32 | 219/147 |
| 5,793,449 A | 8/1998 | Lagerwall | | |
| 5,813,049 A * | 9/1998 | Xu | A61F 9/06 | 2/410 |
| 5,825,441 A | 10/1998 | Hornell | | |
| 5,959,705 A * | 9/1999 | Fergason | A61F 9/067 | 2/8.8 |
| 6,021,520 A * | 2/2000 | Wang-Lee | A61F 9/067 | 2/8.8 |
| 6,035,451 A | 3/2000 | Burns | | |
| 6,097,451 A | 8/2000 | Palmer | | |
| 6,119,266 A * | 9/2000 | Kennedy | A61F 9/06 | 2/8.1 |
| 6,270,223 B1 | 8/2001 | Del Bon | | |
| 6,407,847 B1 * | 6/2002 | Poll | E06B 3/66 | 252/583 |
| 6,424,448 B1 * | 7/2002 | Levy | G02B 23/18 | 359/237 |
| 6,786,610 B2 | 9/2004 | Faris | | |
| 6,910,729 B2 * | 6/2005 | Kraenzler | B32B 17/10036 | 296/146.15 |
| 7,477,330 B2 | 1/2009 | Magnusson | | |
| 2004/0031903 A1 * | 2/2004 | Kiyoshi | A61F 9/067 | 250/201.1 |
| 2004/0117888 A1 | 6/2004 | Wang-Lee | | |
| 2004/0179149 A1 * | 9/2004 | Wang-Lee | A61F 9/061 | 349/58 |
| 2005/0007667 A1 * | 1/2005 | Fergason | A61F 9/067 | 359/601 |
| 2005/0097648 A1 | 5/2005 | Ackermann | | |
| 2006/0007550 A1 * | 1/2006 | Tonar | B60R 1/088 | 359/604 |
| 2006/0010551 A1 * | 1/2006 | Bishop | A61F 9/06 | 2/15 |
| 2006/0203148 A1 * | 9/2006 | Magnusson | G02F 1/133528 | 349/96 |
| 2006/0285330 A1 * | 12/2006 | Sundell | A61F 9/067 | 362/293 |
| 2007/0089215 A1 * | 4/2007 | Biche | A61F 9/067 | 2/8.2 |
| 2007/0131845 A1 * | 6/2007 | Huh | A61F 9/067 | 250/206.1 |
| 2009/0094721 A1 * | 4/2009 | Becker | A61F 9/067 | 2/8.8 |
| 2009/0235420 A1 * | 9/2009 | Chiang | A61F 9/06 | 2/8.5 |
| 2009/0316248 A1 | 12/2009 | Karmhag | | |
| 2010/0060825 A1 * | 3/2010 | Jang | B82Y 20/00 | 349/86 |
| 2010/0090997 A1 * | 4/2010 | Huh | A61F 9/067 | 345/207 |
| 2010/0132086 A1 * | 6/2010 | Huh | A61F 9/067 | 2/8.2 |
| 2010/0212058 A1 * | 8/2010 | Wanhainen | A42B 3/225 | 2/8.2 |
| 2010/0287676 A1 | 11/2010 | Seo | | |
| 2011/0101890 A1 * | 5/2011 | Robinson | A61F 9/064 | 315/320 |
| 2011/0116076 A1 * | 5/2011 | Chantry | A61F 9/06 | 356/51 |
| 2012/0081162 A1 * | 4/2012 | Greiner | A61F 9/067 | 327/171 |
| 2012/0176659 A1 * | 7/2012 | Hsieh | A61F 9/067 | 359/272 |
| 2012/0180180 A1 * | 7/2012 | Steve | A61F 9/067 | 2/12 |
| 2012/0204303 A1 * | 8/2012 | Seo | A61F 9/023 | 2/12 |
| 2013/0026150 A1 * | 1/2013 | Chantry | A61F 9/067 | 219/136 |
| 2014/0320771 A1 * | 10/2014 | Keller | A61F 9/067 | 349/14 |

FOREIGN PATENT DOCUMENTS

| | | | |
|---|---|---|---|
| EP | 2676647 A1 * | 12/2013 | A61F 9/067 |
| KR | 10-0658036 | 12/2006 | |
| WO | WO 2009/045676 | 4/2009 | |

\* cited by examiner

WELDING HELMET HAVING A FILTER ARRANGEMENT

FIELD OF THE INVENTION

The present invention relates to a welding helmet having a filter arrangement, and, in particular, a filter arrangement including a main filter and at least one auxiliary filter.

BACKGROUND

Welding helmets fitted with a filter for protecting welders from optical radiation generated during welding operations are well known. A typical welding helmet filter is a device disposed in an aperture in the front of a welding helmet that a welder can look through to view welding operations, without their eyes being exposed to harmful amounts of optical radiation.

The visible band of electromagnetic spectrum, that is the range of optical radiation that can be detected by the human eye, is generally understood in the welding industry to be the band of wavelengths from approximately 380 to 780 nanometres (nm). A further band of wavelengths of optical radiation having wavelengths shorter than the visible band is often referred to as ultraviolet (UV) radiation. The part of UV radiation spectrum that is of interest in the welding industry is approximately 200 nm to 380 nm. A further band of wavelengths of optical radiation having wavelengths longer than the visible band is often known as infrared radiation (IR). The part of IR radiation spectrum that is of interest in the welding industry is approximately 780 nm to 3000 nm.

Ultraviolet and infrared radiation often generated by a welding arc during welding processes can be harmful to the human eye, potentially causing irreversible damage. Further, the visible radiation generated by welding processes is often too bright to be comfortable for the welder to observe directly and hence a means of attenuating the transmission of this visible radiation is desirable. Generally, the human eye is protected from bright visible radiation by normal aversion response, such as blink reflex or head movement, however, in some circumstances, bright visible radiation can dazzle the welder and cause temporary blindness.

Known welding helmet filter types include passive filters or automatically darkening filters (ADFs). A passive filter is often a dark coloured, usually green, glass lens which allows a limited range of wavelengths of radiation to pass through with a certain level of transmittance. A passive filter is often rather dark and provides its user with only a limited amount of visibility in normal ambient light conditions and as such is usually positioned in front of the welders face immediately before the welder starts the welding operation. A traditional ADF has a default state that is a light state, such that the welder has good forward visibility. It automatically changes to a darker state at the start of welding operations and returns to the light state when the welder ceases the welding operations. Often, ADFs use switchable electro-optical technologies such as liquid crystal technology to provide these different states. Examples of liquid crystal technology for use in an ADF are described in U.S. Pat. Nos. 6,097,451, 5,825,441, and 7,477,330.

Generally available welding helmet filters have a certain shade or range of shades or shade numbers. Shade S is related to luminous transmittance, TL (expressed as a fraction of light passing through a filter with respect to a standard light source and a standard observer) by the following equation:

$$S = 1 + (7/3) \cdot {}^{10}\log(1/TL)$$

Here, TL is defined as the ratio of transmitted luminous intensity to the incident luminous intensity. A precise definition of luminous transmittance is given in various standards, for example the European standard for Personal Eye Protection—Transmittance requirements, EN 169:2002. For given shade numbers, the tolerance in luminous transmittance and maximum transmittance for different wavelength bands of UV and IR radiation are usually specified by industrial standards that are applied to welding filters. For example, shade three (3), in the European standard for Personal Eye Protection—Transmittance requirements, EN 169:2002, specifies a luminous transmittance level of between 8.5 and 17.8%. By way of further example, shade twelve (12) specifies a luminous transmittance level of between 0.0012 and 0.0032%. For shade 12, a maximum permitted UV transmittance at wavelengths between 313 nm and 365 nm is 0.0012% and a maximum allowable mean spectral IR transmittance for the band of wavelengths from 780 to 1400 nm is 0.027%. The maximum UV and IR transmittance values specified for the darkest possible shade for a particular filter (e.g., shade 12) must also hold also for the lightest shade (e.g., shade 3).

The shade of a typical passive filter for arc welding is shade ten (10). The shade of a typical ADF during the light state shade 3, whereas the shade in the dark state can often be pre-selected by the welder and is typically in the range between shade eight (8) and shade twelve (12). The dark state shade is chosen depending on the type of welding operation being conducted and personal preference or comfort of the welder.

Providing welding helmets fitted with an ADF allows the welder to have some vision whilst they are not welding without having to raise the face shield or remove the welding helmet, however, it does not take account of the welder's peripheral vision. More recently, some welding helmets have been fitted with passive side filters, often known as side windows to improve the welder's peripheral vision. These side windows are passive filters that reduce the level of visible radiation that is transmitted to the welder. Typically, the transmittance of currently available passive filters is comparable to a level between the dark and light states of automatically darkening welding filters. The shade or level of transmittance chosen is a balance between allowing sufficient visible radiation transmittance to improve the welder's peripheral vision and minimizing the amount of visible radiation entering the helmet that could cause glare or internal reflections on the main filter during welding operations. Welding helmets with such side windows are described in U.S. Pat. No. 5,191,468.

Other side window configurations known in the art, for example, those described in US 2004/0117888, include transparent side windows covered with doors that can be opened when the welder is not performing welding operations and closed manually by the welder prior to welding operations. The side windows are typically located on either side of the main filter, that is the filter in the front of the welding helmet that the welder uses for viewing welding operations, and therefore can improve the welder's peripheral vision when the welder is not welding.

Side windows improve welder's peripheral vision and awareness considerably. However there are certain situations where the functionality of a welding helmet with passive side windows may be further improved to better meet the needs of a welder. For example, further optimizing a welder's peripheral vision can greatly improve the welder's experience of use of the helmet and the welding process.

SUMMARY

The present disclosure is directed to welding helmets having a filter arrangement, which includes a main filter and at least one auxiliary filter. At least one auxiliary filter is separate from and positioned next to the main filter. At least one auxiliary filter includes an electro-optic element adapted to attenuate transmission of optical radiation incident on the auxiliary filter.

In some embodiments, the main filter also may include an electro-optic element. In exemplary implementations of such embodiments, the electro-optic element of the main filter may include a liquid crystal material and at least one auxiliary filter may include an electrochromic material.

In some embodiments, at least one auxiliary filter may be adapted to be switched independently from the main filter, in coordination with the main filter or both.

An exemplary welding helmet according to the present disclosure may include at least two auxiliary filters, at least one being disposed on each side of the main filter. At least two auxiliary filters may be configured to be switched independently from each other.

An exemplary welding helmet according to the present disclosure may include a first face shield and a second face shield movably attached to the first face shield. The main filter may be disposed in an aperture of the second face shield. One or more auxiliary filters may be disposed in the first face shield, the second face shield or both.

BRIEF DESCRIPTION OF THE DRAWINGS

By way of example only, embodiments of the present disclosure will now be described below with reference to the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawing that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure provides one or more auxiliary filters including one or more electro-optic elements adapted to attenuate transmission of incident optical radiation. Some exemplary auxiliary filters may be characterized by at least two states. A light state may be provided to increase peripheral vision and awareness of the surroundings and a dark state may be provided to reduce visible radiation entering the welding helmet through the auxiliary filters during welding operations, or if welding is taking place nearby in the peripheral field of vision.

Electro-optic elements according to the present disclosure include a layer of optically responsive medium capable of changing, in response to applied voltage, at least one of its optical properties that influence the amount of light transmitted through the electro-optic element. For example, when voltage is applied to the optically responsive medium, this may cause a change in one or more of reflectivity, transmittance, absorption, polarization state, etc., of the light incident on the optically responsive medium.

Figure 1:
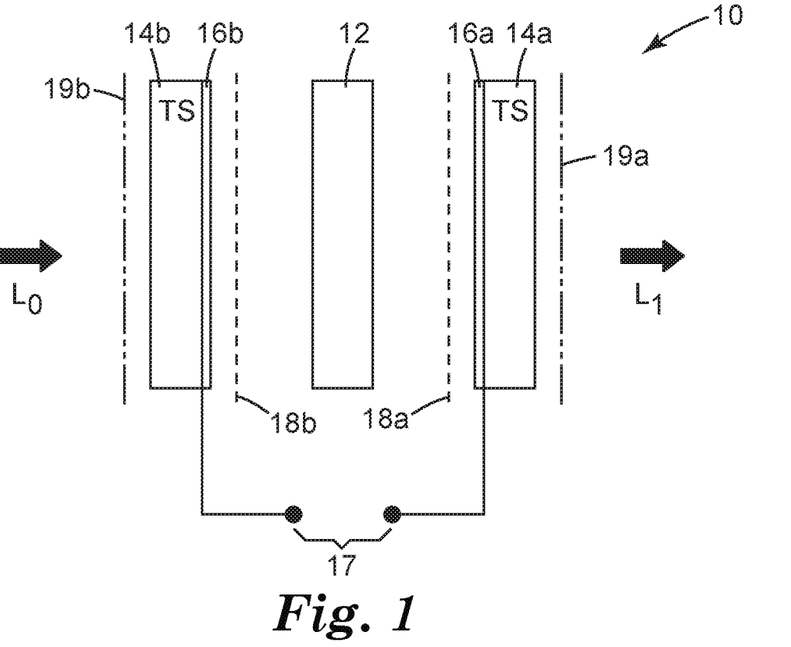
FIG. 1 illustrates schematically an exemplary configuration of an electro-optic element according to the present disclosure.

FIG. 1 illustrates schematically one exemplary configuration of such an electro-optic element 10, which includes an optically responsive medium 12 disposed between transparent substrates 14a and 14b. Transparent substrates may be constructed from any suitable material having a degree of clarity sufficient for a particular application. Examples of suitable materials are glass and transparent plastic materials, such as polycarbonate. The electro-optic element 10 further includes transparent conductive layers 16a and 16b configured to apply voltage 17 to the optically responsive medium 12. The conductive layers 16a and 16b may be disposed on the transparent substrates 14a and 14b, respectively.

One preferred type of optically responsive media suitable for use in embodiments of the present disclosure is liquid crystal materials. Such electro-optic elements may be referred to as liquid crystal cells. When liquid crystal materials are comprised in the optically responsive medium 12, the electro-optic element 10 also typically includes one or more polarisers 19a and 19b, which may be disposed on the outer sides of the transparent substrates 14a and 14b, with respect to the optical medium. Alternatively, each polarizer 19a and 19b may be disposed between the optically responsive medium 12 and the transparent substrate 14a or 14b, as applicable.

As used in this specification, the term "polarizer" means a polarizing filter that transmits light having a first polarization and absorbs and/or reflects light having a second polarization, which is different from the first polarization. Depending on the type of the liquid crystal material used in the optically responsive medium, polarizers 19a and 19b may be linear polarizers arranged with their transmission axes crossed or orthogonal with respect to each other, parallel to each other or having another suitable orientation. Liquid crystal-based electro-optic elements may further include one or more alignment layers, such as 18a and 18b, for facilitating a desired orientation of the liquid crystal material. One or more alignment layers 18a and 18b are typically disposed adjacent to and in contact with the optically responsive medium 12. In some exemplary embodiments, one or more alignment layers may also serve as polarizers.

Certain types of liquid crystals, such as nematic liquid crystals, change their orientation in response to applied electric field, thereby also changing the refractive index profile, and, particularly, birefringence of the medium. In liquid crystal cells utilizing twisted nematics, the nematic molecules are arranged in specific angular positions (typically, due to alignment layers) so that the molecules are twisted through their respective twist angle between the transparent substrates 14a and 14b. The orientation of nematic liquid crystal molecules can be controlled by applying an electric field between the transparent electrodes 16a and 16b.

With further reference to FIG. 1, when no voltage is applied to a twisted nematic liquid crystal cell, the polarization plane of the incident light L0 that has been polarized by the input polarizer 19b is rotated as light passes through the optically responsive medium 12 (here, twisted nematic material). If the output polarizer 19a is aligned with the output polarization of light exiting the optically responsive medium 12, the opto-electronic device 10 remains transparent with the amount of the transmitted light L1 being relatively high. Application of a voltage 17 creates an electric field between the transparent electrodes 16a and 16b. The nematic liquid crystal molecules then reorient to align with the electric field, perpendicular to the electrodes 16a and 16b. As a result, the polarization plane of the light transmitted through the optically responsive medium 12 does not experience as much rotation and at least a portion of that light is blocked by the output polarizer 19a. The amount of the transmitted light L1 in this case is lowered, and the electro-optic device 10 achieves a darkened or attenuated state. Thus, when a voltage is applied to the twisted nematic liquid crystal cells, an attenuation effect is obtained. The degree of rotation of the nematic molecules may be controlled by varying the applied voltage, and thus the corresponding attenuation effect may also be controlled.

In the exemplary embodiments described above, the liquid crystal cell will be in a light state in the absence of an applied voltage and in a dark state in the presence of an applied voltage. However, in other exemplary embodiments, the reverse may be the case. Generally, when electric field is applied to the liquid crystal optically responsive medium, the liquid crystal material reorients resulting in altered transmission properties of polarized light. For example, incident light L0 can be polarized by a first polarizer 19b and its polarization can be then reoriented by the liquid crystal optically responsive medium 12 to not coincide with the transmission axis of a second polarizer 19a, in which case the second polarizer 19a would pass only an attenuated amount of light L1.

Figure 2:
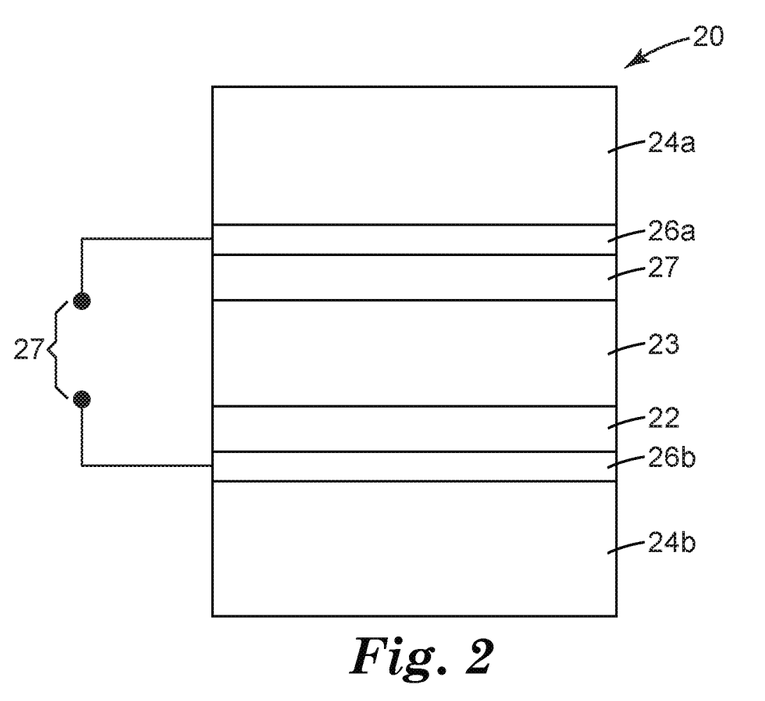
FIG. 2 illustrates schematically another exemplary configuration of an electro-optic element according to the present disclosure.

Another preferred type of optically responsive media suitable for use in embodiments of the present disclosure are electrochromic materials. FIG. 2 illustrates schematically one exemplary configuration of such an electro-optic element 20, which includes an optically responsive medium. In this exemplary embodiment, the optically responsive medium comprises a layer of electrochromic material 22 disposed between transparent substrates 24a and 24b. The electro-optic element 20 further includes transparent conductive layers 26a and 26b disposed between the electrochromic material 22 and the transparent substrate 24a or 24b, as applicable. An ion conductor layer 23 may be provided between the electrochromic material 22 and the conductive layer 26a, and an ion storage layer 27 may also be provided between the ion conductor layer 23 and the conductive layer 26a. The transparent conductive layers are configured to apply an electric field, for example, via application of voltage 27, to the electrochromic material 22. The conductive layers 26a and 26b may be disposed on the transparent substrates 24a and 24b, respectively.

When voltage is applied to the transparent conductive layers 26a and 26b, ions are transferred between the electrochromic, ion conductor and ion storage layers. As a result, a chemical reaction occurs in the electrochromic material 22 thus changing the optical properties of the material. In this exemplary embodiment, application of voltage would result in a chemical reaction that would change the amount of light transmitted by the electrochromic material 22. In one embodiment, application of voltage would change the amount of light absorbed by the electrochromic material. The electrochromic material 22 may be initially opaque and changed to a more transparent state as a result of applied voltage, or vice versa (i.e., the electrochromic material 22 may be initially transparent and changed to a more opaque state as a result of applied voltage). Examples of suitable electrochromic materials include oxides based on wolfram or nickel and various other materials. The ion conductor layer 23 may be or include a liquid or a polymer electrolyte. With electrochromic materials, a reverse voltage is needed to cause the optically responsive medium to switch back to an initial state. Hence, electrochromic technology can be very energy efficient as it may only require energy to switch from one state to another.

Figure 3:
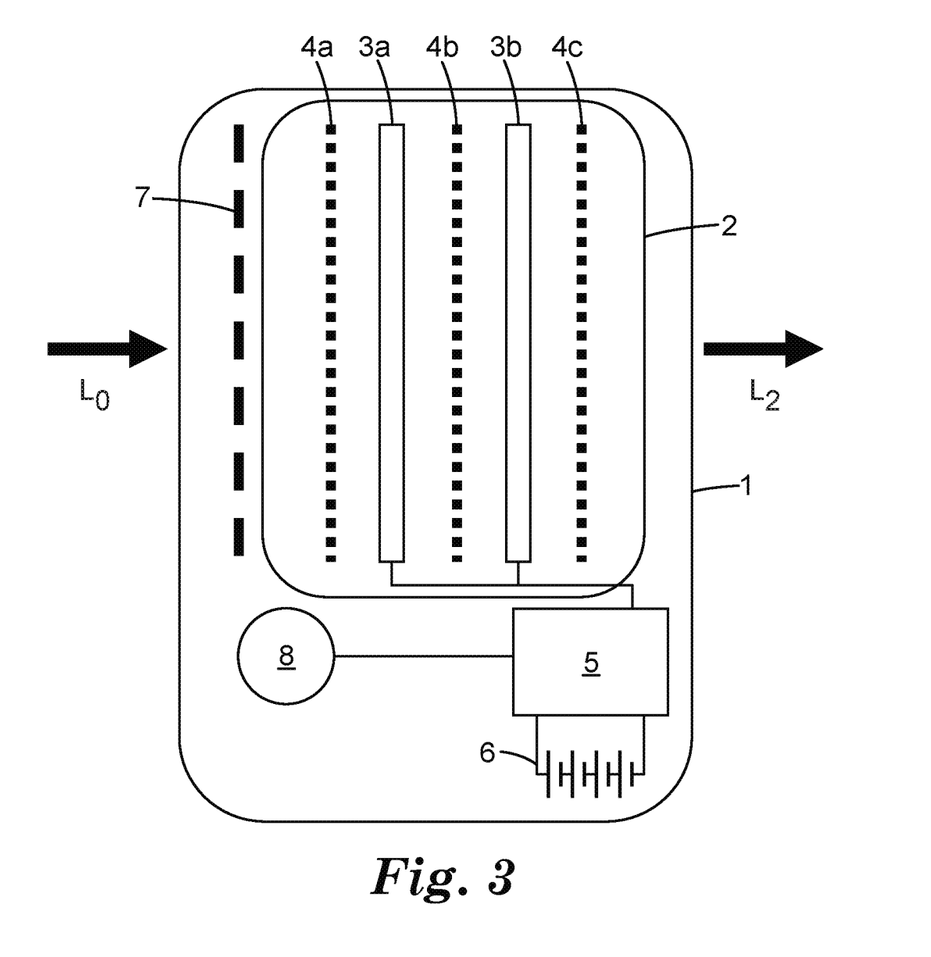
FIG. 3 is a diagrammatic illustration of an auto darkening filter (ADF) suitable for use with exemplary embodiments of the present disclosure.

FIG. 3 is a diagrammatic illustration of an exemplary auto darkening filter (ADF) suitable for use with embodiments of the present invention. The auto darkening filter 1 comprises an exemplary electro-optic element 2. In this embodiment, the electro-optic element 2 includes two or more liquid crystal cells 3a and 3b, preferably arranged alternately with polarisers 4a, 4b, 4c. One or both the liquid crystal cells may have the configuration described in reference to FIG. 1 or another suitable construction. An electronic controller 5, which is in electrical communication with one or both of the liquid crystal cells 3a and 3b is configured to provide the liquid crystal cells 3a, 3b with an appropriate electrical signal to align or at least partially align the liquid crystal molecules. As explained above, by changing the alignment of the liquid crystal in the liquid crystal cells 3a, 3b in combination with the polarising filters 4a, 4b, 4c, the transmission of visible radiation L0 incident on the auto darkening filter 1 may be attenuated to a lesser value L2. The direction of polarisation of the polarisers is typically arranged such that alternate filters have a pass axis at 90 degrees to a neighbouring polarizer. In this example, the pass axis of the middle polarising filter 4b may be horizontally aligned and the pass axes of the two outer polarising filters 4a, 4c may be vertically aligned. However, other respective angles and orientations are within the scope of the present disclosure.

A power source 6 may be included to provide power to the electronic controller and subsequently to the liquid crystal cells. The power source 6 may include a battery formed from primary cells. Alternatively or additionally, the power source 6 may include photovoltaic cells, often known as solar cells, arranged such that ambient visible radiation or visible radiation from the welding operations is converted to electrical power for powering the electronic controller and electro-optic elements. Combinations of photovoltaic cells and batteries also may be used.

The exemplary auto darkening filter 1 may include an optional interference filter 7 for the purpose of reflecting a substantial amount of infrared radiation and ultraviolet radiation. The interference filter may include a transparent substrate that is coated with alternating layers having different composition, for example, a dielectric material and a metal. In addition to filtering the infrared radiation and ultra violet radiation, such an interference filter 7 may have the effect of reducing the band of wavelengths of visible radiation that are transmitted to the welder.

The electronic controller 5 that drives the one or more liquid crystal cells 3a, 3b may comprise a welding detector 8 that is configured to detect a welding arc. The welding detector 8 determines when a welding operation is initiated. For example, the welding detector may include a photodiode, such as s silicon photodiode, and electronics with a logic function for processing signals detected by the photodiode. Once the welding detector 8 has detected initiation of a welding operation, that information is transmitted to the controller 5, which triggers the auto darkening filter 1 to switch from a light state to a dark state, which is a state characterized by a higher degree of attenuation of incident visible radiation than the light state.

In the welding industry, a light state is typically characterized by a shade of about 3 to about 4, while a dark state is typically characterized by a shade of about 8 to about 13. In some embodiments, a light state can be shade 3 with a dark state selectable by the user between shades 8 and 12 (i.e., 8, 9, 10, 11, or 12). In other embodiments, a light state can be shade 4 with a dark state selectable between shades 9 and 13 (i.e., 9, 10, 11, 12 or 13). In yet other embodiments, dark state may be characterized by shade 5 or 6, such as for gas welding and grinding applications. In general, any suitable shades associated with light states and dark states are within the scope of the present disclosure, which may be selected depending on the welding method, welding current used and the location of the auto-darkening filter.

The switching speed of the auto darkening filter 1, that is, the time between the ignition of a welding arc and the auto darkening filter 1 reaching its fully dark state, is often very short. Depending on the technology of the ADF and the environment, the switching speed of the auto darkening filter 1 may be on the order of approximately 0.1 millisecond (ms) or another suitable time period. In some embodiments, a delay may be introduced between the time when the welder stops the welding operation and the auto darkening filter 1 returning to the light state. The delay may be between 100 ms and 250 ms, or another suitable time period depending on the technology of the ADF, to ensure that the level of visible radiation emitted from the weld has reduced to a desirable level before exposing the welder to it.

Although the ADF 1 has been described in reference to the electro-optic element 2, those of ordinary skill in the art will readily appreciate that other configurations of the electro-optic element may be used. For example, the ADF 1 may be configured with any of the electro-optic elements described in connection with FIGS. 1 and 2.

The above described auto darkening filters are suitable for use in welding helmets as main filters or as auxiliary filters. The concepts of main and auxiliary filters can be further understood explained in with reference to FIG. 4, which illustrates schematically an exemplary welding helmet 100 worn by a user 1, including a main filter 102, an auxiliary filter 104 disposed next to and on one side (here, left) of the main filter 102 and an additional auxiliary filter 106 disposed next to and on another side (here, right) of the main filter 102. For the purposes of the present disclosure, the terms "side," "left," "right," "above," "below," "front," and other similar terms are used to describe spatial relationships of the filters when a welding helmet containing them is worn by a user. In the working position, the main filter 102 is disposed in front of the eyes 2a and 2b of the user 1, such that both of the user's eyes 2a and 2b are looking through the main filter 102, and, preferably, in the direct line of vision 103 of the user 1. Direct line of vision 103 is defined as the space between the visual axes 103a and 103b drawn from the center of and orthogonal to each eye of the user 1, represented by a standardized head form. The direct line of vision 103 includes an area of overlap between the central parts 101 of the user's vision from both eyes 2a and 2b.

Figure 4:
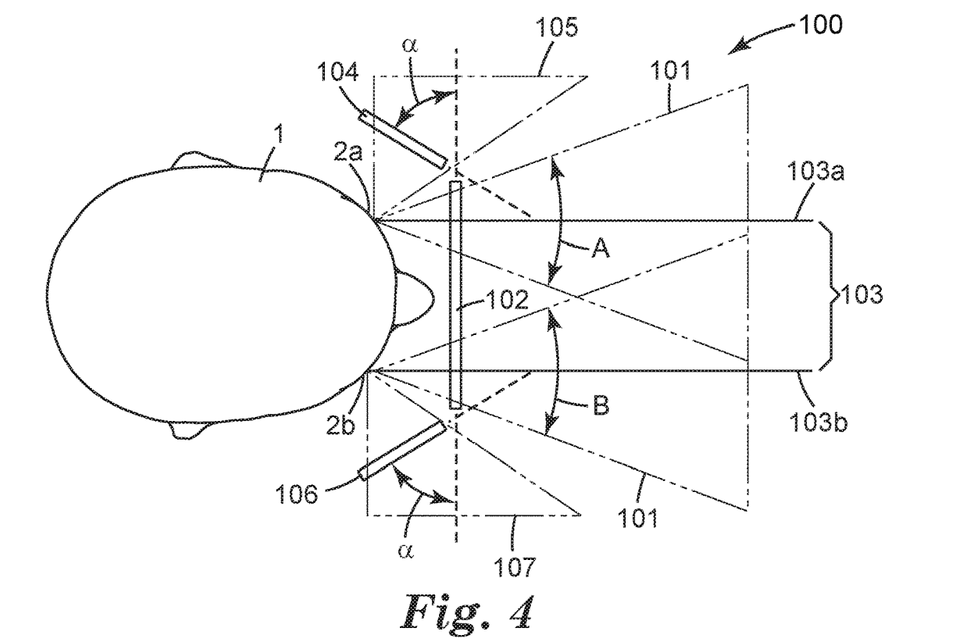
FIG. 4 illustrates schematically an exemplary filter arrangement according to the present disclosure.

The auxiliary filters 104 and 106 are separate from but are disposed next to, and, preferably, adjacent to the main filter 102. The exemplary auxiliary filters 104 and 106 are disposed not to overlap with the direct line of vision 103 of the user 1. In some embodiments, the auxiliary filters 104 and 106 are disposed not to overlap with the central part of vision 101. Preferably, the auxiliary filters 104 and 106 are disposed the in the peripheral vision areas 105 and 107, respectively, of the user 1. The peripheral vision areas 105 and 107 may be defined as the field of view outside the cones A and B of 45° drawn from the center of each eye 2a and 2b (as can be determined when an exemplary embodiment is mounted on a standardized head form) around the visual axes 103a and 103b, respectively. In some exemplary embodiments, the auxiliary filters 104 and 106 may each form a non-zero angle α with respect to the main filter 102 as measured in a horizontal plain containing the centers of the viewer's eyes 2a and 2b. Typically the angle α is between about 45 degrees and about 90 degrees. However, other values of the angle α are within the scope of the present disclosure, including but not limited to 0, 45 and 90 degrees.

Figure 5:
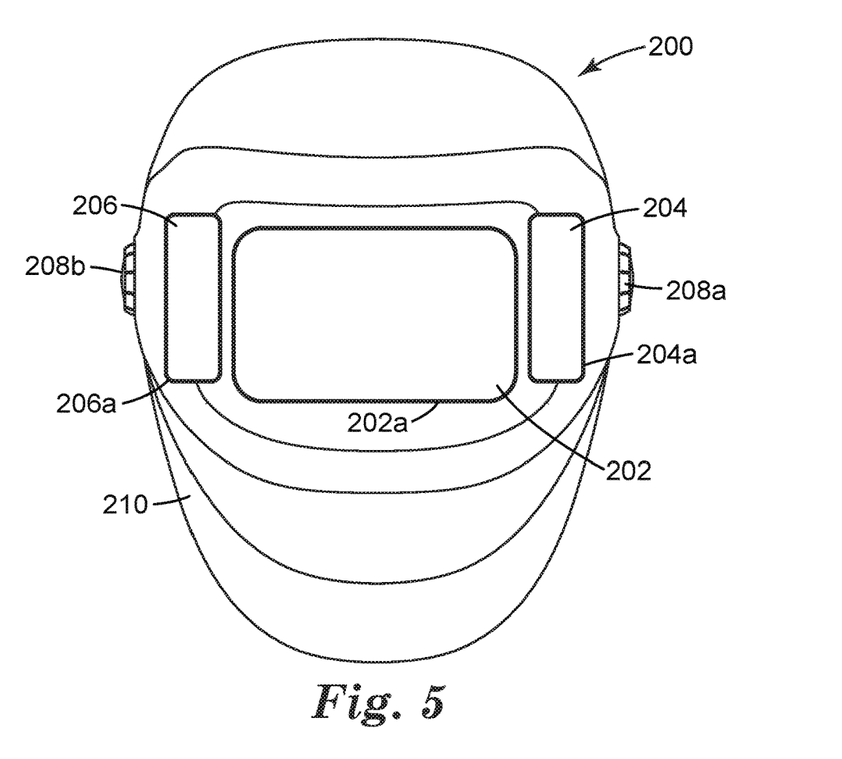
FIG. 5 is a diagrammatic illustration of a welding helmet according to an exemplary embodiment of the present disclosure.

FIG. 5 is a diagrammatic illustration of a welding helmet 200 according to another embodiment of the present disclosure. The welding helmet 200 has a face shield 210 and a head harness (not shown) fitted internally to the face shield 210. The face shield 210 is shaped to cover at least the eyes of a welder, and, preferably, at least the face of a welder. In some exemplary embodiments, the face shield 210 also covers welder's ears, such as the welding shield shown in FIG. 5. The face shield 210 can be made from any suitable non-transparent material. Preferably, the transmittance of the material of the welding shield is lower than what is required for the dark shade of the main filter. One exemplary method of making the face shield 210 includes injection moulding a thermo-plastic material, where the material is black in colour and has the properties of being lightweight, having a high resistance to melting and good flame retardancy properties. The face shield 210 may be provided with a matt surface finish on the inside of the face shield to reduce internal reflections.

The head harness (not shown) may include any device suitable for retaining the face shield on a user's head and can be configured in any suitable way, including those known to those skilled in the art. One exemplary harness includes a band of plastic material with a means for adjusting the circumferential dimension such that it can be secured to the head of the welder and tightened to be held comfortable in place. The face shield 210 is typically attached to the head harness by two pivot mechanisms 208a and 208b, on the outer opposing surfaces of the head harness at the sides of the welder's head between the temples and the ears. The pivot mechanisms allow the face shield 210 to be raised out of view of the welder when not in use, and lowered prior to the welder performing welding operations, such that the face shield 210 can be placed between the welder's face and the arc to prevent optical radiation from the welding operations from directly reaching the welders eyes, and, preferably, also face and ears.

The exemplary welding helmet shown in FIG. 5 includes a main filter 202 arranged in a first aperture 202a located in the front of the face shield 210 and auxiliary filters 204 and 206 arranged in second and third apertures 204a and 206a, respectively, in the face shield 210. Auxiliary filters 204 and 206 are located on either side (left and right) of the main filter 202 and next to it. One auxiliary filter 204 or 206 is disposed on either side of the main filter 202, such that the peripheral vision of the welder is extended. As explained above, the auxiliary filters 204 and 206 are individual constructions and are separate from the main filter 202. The main filter 202 in the front aperture is arranged such that when the welder is performing welding operations, he or she can view the point of welding through the filter 202. It is important that the main filter 202 is fitted in a manner so that unattenuated visible radiation generated by the welding operating does not directly reach the eyes of the welder.

Any one or more of the main filter 202 and the auxiliary filters 204 and 206 can comprise one or more electro-optic elements described above. In one exemplary embodiment, each of the auxiliary filters 204 and 206 includes an electro-optic element. Thus, one or more of the main filter 202 and the auxiliary filters 204 and 206 are switchable between at least two states, a first state being different from a second state. The first state may be a light state and a second state may be a dark state, which is a state characterized by a higher degree of attenuation of incident visible radiation than the light state. The level of visible radiation that is transmitted through the auxiliary filters 204 and 206 in the light state is typically about shade 2 to 4 and the shade in the dark state may be from shade 6 to shade 12 or higher. Other shade levels are, however, within the scope of the present disclosure. Shade 5, for example, may be considered a dark state shade or a light state shade, depending on the application.

In one exemplary embodiment, an auxiliary filter may have only one light shade (e.g., 2 to 3) and only one dark shade (e.g., 7 to 10). In other exemplary embodiments, the dark shade of an auxiliary filter may be selected by the welder. One way a welder could select a shade is by pressing an appropriate button on a user interface, located next to the main filter, an auxiliary filter, or at another suitable location. The shade thus may be chosen depending on the personal preference of the welder and how much visible radiation transmission through the auxiliary filters is expected or desired. In embodiments where both the main filter 202 and the auxiliary filters 204 and 206 include electro-optic elements, the shades associated with a dark state and a light state of the main filter may be the same or different as a dark state and a light state of the auxiliary filters. In yet other exemplary embodiments, one or more filters may be passive or otherwise kept at a permanent shade.

The switching speed of the auxiliary filters may not need to be as fast as the switching speed of the main filter 202 as the welder is not intended to be viewing the welding operations through the auxiliary filters 204 and 206. However, the switching speed needs to be fast enough that visible radiation transmitted inside the welding helmet via the auxiliary filters 204 and 206 does not cause internal reflections that dazzle the welder at the start of a welding operation. In an exemplary embodiment, an auxiliary filter switching speed may be in the range of 1 ms to 5 ms. If the level of visible radiation incident on a welding detector associated with an auxiliary filter 204 or 206 does not meet the criteria for welding light, the auxiliary filter will remain in the light state allowing the welder better awareness of his or her surroundings during the welding operation.

In some exemplary embodiments, the state of each of the auxiliary filters 204 and 205 may be controlled separately and independently from each other and separately and independently from the main filter 202. In one embodiment, when the welder is getting ready to perform a welding operation, the main filter 202 and the auxiliary filters 204 and 206 may be in the light state and the welder has both good visibility of the area in front of the main filter 202 and also good vision of and improved awareness of the surroundings. The light state of the auxiliary filters 204 and 206 may be the same shade or a lighter shade than the light state of the main filter 202 and as such the welder's peripheral vision is further optimised and gives better vision than passive side windows that generally need to have a higher or darker shade than the main filter's light state. If a second welder is performing a welding operation to one side of the welder, the auxiliary filter on the side of the second welder may darken to a dark state if the visible radiation level from the second welder's welding operation meets a predefined criterion, regardless of the state of the main filter 202. Hence, the auxiliary filters 204 and 206 only switch to the dark state when the visible radiation level incident on them is at a level where it is desirable for them to darken.

Figure 6A:
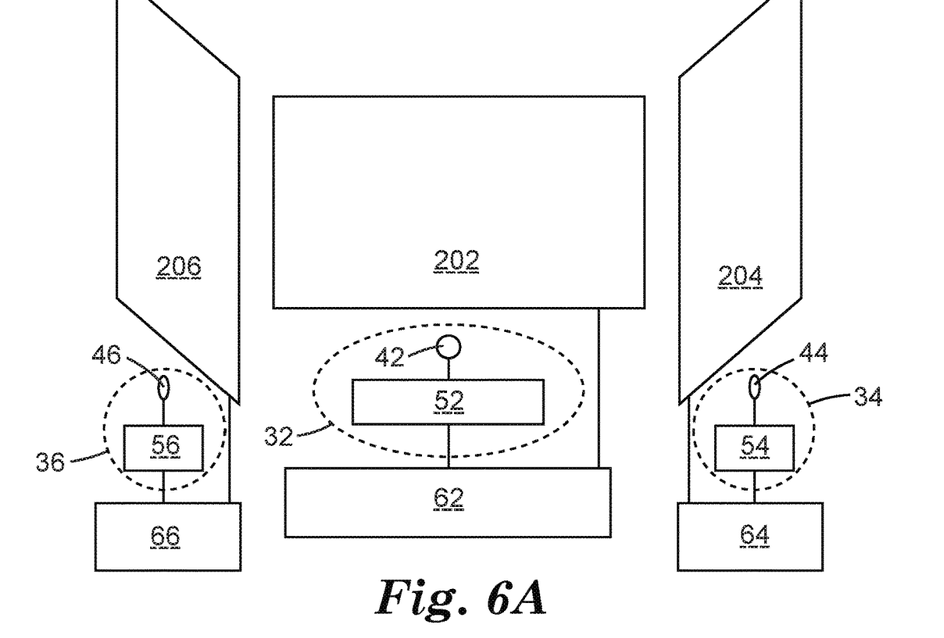
FIGS. 6A, 6B and 6C illustrate schematically filter arrangements allowing the main filter and auxiliary filters to be switched in coordination or separately.

FIG. 6A illustrates an exemplary filter arrangement such that the auxiliary filters 204 and 206 may be switched independently from each other and independently from the main filter 202. In this exemplary embodiment, each filter has a separate associated welding detector and a separate associated electronic controller. A first welding detector 32 and a first electronic controller 62 are associated with the main filter 202. The first welding detector 32 includes a first sensor 42 (such as a photodiode) and first electronics with a logic function 52 for processing the signals from the first sensor 42 and determining whether the signals reaching the main filter 202 and the first sensor 42 satisfy one or more criteria. Based on this determination, the first controller 62 may cause the main filter 202 to enter a dark state or remain in a light state. Similarly, a second welding detector 34 and a second electronic controller 64 are associated with the auxiliary filter 204. The second welding detector 34 includes a second sensor 44 (such as a photodiode) and second electronics with a logic function 54 for processing the signals from the second sensor 44 and determining whether the signals reaching the auxiliary filter 204 and the second sensor 44 satisfy one or more predefined criteria. Likewise, a third welding detector 36 and a third electronic controller 66 are associated with the auxiliary filter 206. The third welding detector 36 includes a third sensor 46 (such as a photodiode) and third electronics with a logic function 56 for processing the signals from the third sensor 46 and determining whether the signals reaching the auxiliary filter 206 and the third sensor 46 satisfy one or more predefined criteria. Thus, in this exemplary embodiment, each filter can lighten and darken independently from other filters.

Figure 6B:
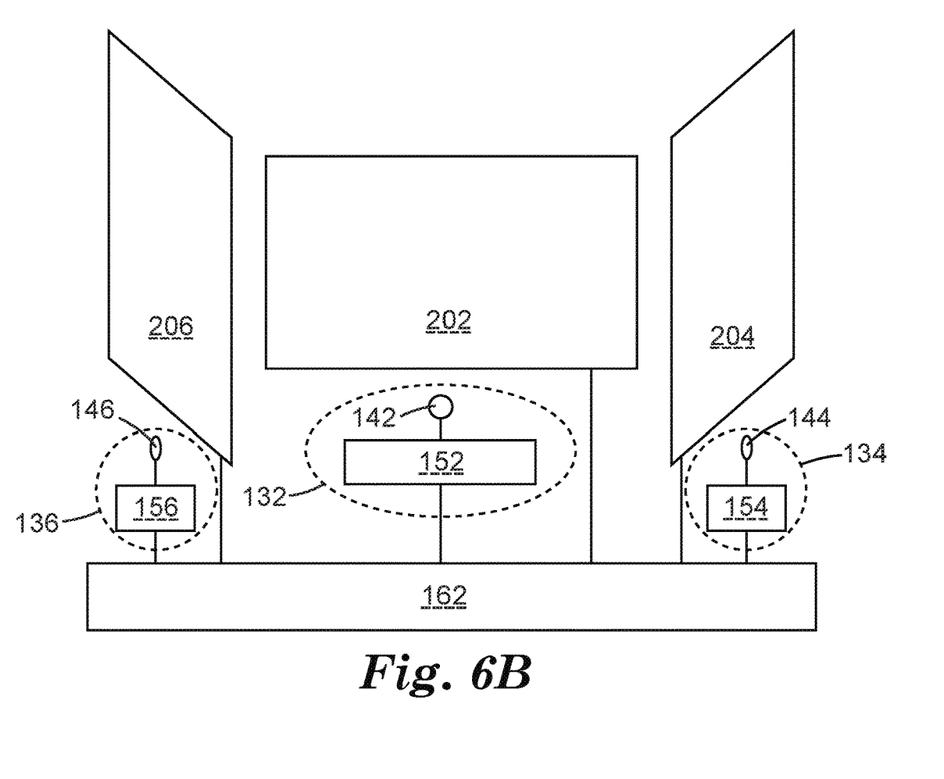

Alternative to the embodiment described above, it may sometimes be desirable for the auxiliary filters 204 to be controlled in coordination with each other, and/or in coordination with the main filter 202. In this case there may be an electrical connection between the electronic controllers of the filters to synchronise the switching of the filters or they may have a common electronic controller. FIG. 6B illustrates such an exemplary filter arrangement. In this exemplary embodiment, each filter has a separate associated welding detector and a common electronic controller 162. A first welding detector 132, associated with the main filter 202, includes a first sensor 142 (such as a photodiode) and first electronics with a logic function 152 for processing the signals from the first sensor 142 and determining whether the signals reaching the main filter 202 and the first sensor 142 satisfy one or more criteria. Similarly, a second welding detector 134, associated with the auxiliary filter 204, includes a second sensor 144 (such as a photodiode) and second electronics with a logic function 154 for processing the signals from the second sensor 144 and determining whether the signals reaching the auxiliary filter 204 and the second sensor 144 satisfy one or more predefined criteria. Likewise, a third welding detector 136, associated with the auxiliary filter 206, includes a third sensor 146 (such as a photodiode) and third electronics with a logic function 156 for processing the signals from the third sensor 146 and determining whether the signals reaching the auxiliary filter 206 and the third sensor 146 satisfy one or more predefined criteria.

The inputs from the first, second and third welding detectors 132, 134 and 136 are processed by the common electronic controller 162 to control the state of the main filter 202 and the auxiliary filters 204 and 206. In some embodiments, it is desirable that the main filter 202 is the dominant filter (i.e., both the main filter 202 and the auxiliary filters 204 and 206 are darkened in response to the appropriate signals from the first welding detector 132) to ensure that the welder is not exposed to an unnecessarily high level of visible radiation in their forward range of vision. Additionally or alternatively, the main filter 202 may be provided with a means for ensuring that the main filter 202 is not switched at a time when it is not necessary or desired. For example, the electronic controller 162 may cause the main filter 202 to darken only when welding is detected in the forward direction (e.g., only by the first detector 132). In turn, one or both of the auxiliary filters 204 and 206 may become dark when a welding operation is detected on a particular auxiliary filter's side, e.g., by detector 134 or 136. However, this exemplary arrangement can also provide for the independent switching of the auxiliary filters and/or the main filter, as described in connection with FIG. 6A.

Figure 6C:
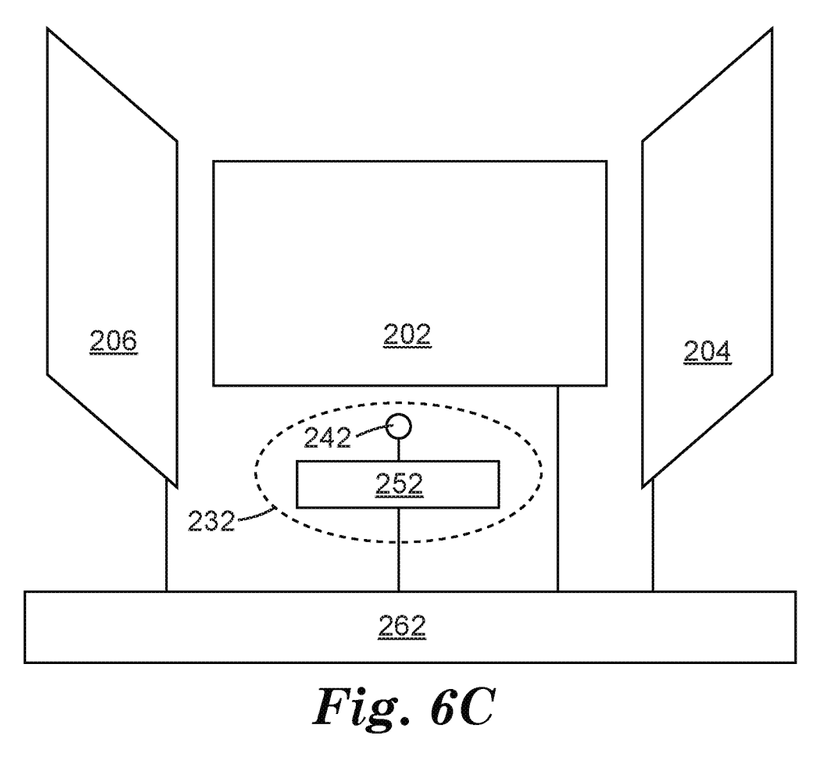

Another exemplary embodiment where the main filter 202 and the auxiliary filters are controlled in coordination is shown in FIG. 6C. In this exemplary embodiment, only the main filter 202 has an associated welding detector 232 and an electronic controller 262. The welding detector 232 includes a sensor 242 (such as a photodiode) and electronics with a logic function 252 for processing the signals from the sensor 242 and determining whether the signals reaching the main filter 202 and the sensor 242 satisfy one or more criteria. The input from the welding detector 232 is processed by the electronic controller 262 to control the state of the main filter 202 and the auxiliary filters 204 and 206. Thus, the electronic controller 262 may cause one or more or all of the filters to darken when welding is detected in the forward direction.

Electro-optic elements comprised in one or more of the filters may use any suitable optically responsive media. In one exemplary embodiment, the filters (both the main filter 202 and the auxiliary filters 204 and 206) include one or more liquid crystal cells. Typically, liquid crystal cells include glass substrates. Glass substrates can have a high optical clarity. Whilst it is desirable for the main filter 202 to have very good optical clarity, in some embodiments, it may not be as important that the auxiliary filters 204 and 206 have the same high level of optical clarity as the welder is not intended to be viewing welding operations through the auxiliary filters. Hence, the auxiliary filters 204 and 206 may be alternatively made other types of substrates, such as plastic materials.

In other exemplary embodiments, the main filter 202 can include a first type of optically responsive medium, while at least one of the auxiliary filters 204 and 206 may include a second type of optically responsive medium, which is different from the first type. In one embodiment, the first type of optical medium includes a liquid crystal material, while the second type of optically responsive medium includes an electrochromic material.

Figure 7A:
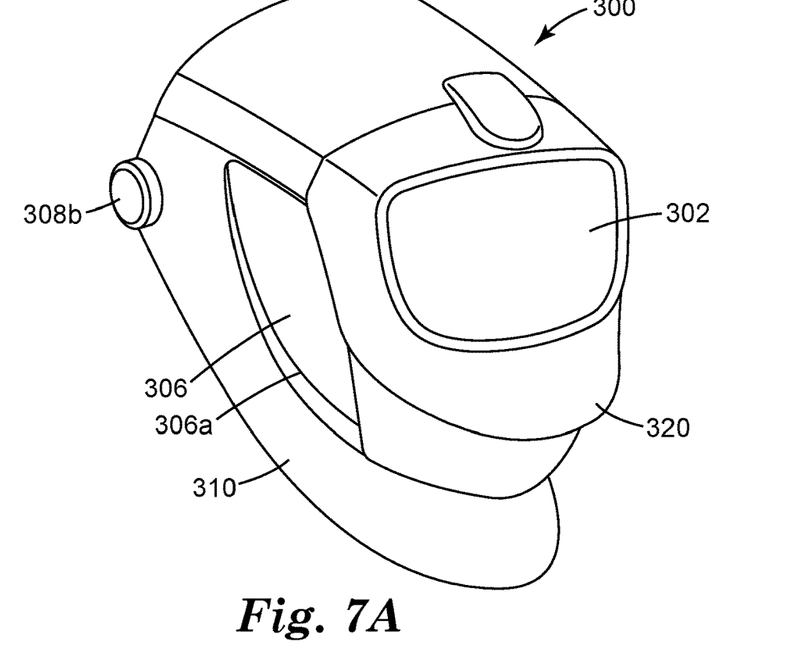
FIGS. 7A and 7B illustrate a welding helmet according to another exemplary embodiment of the present disclosure.
Figure 7B:
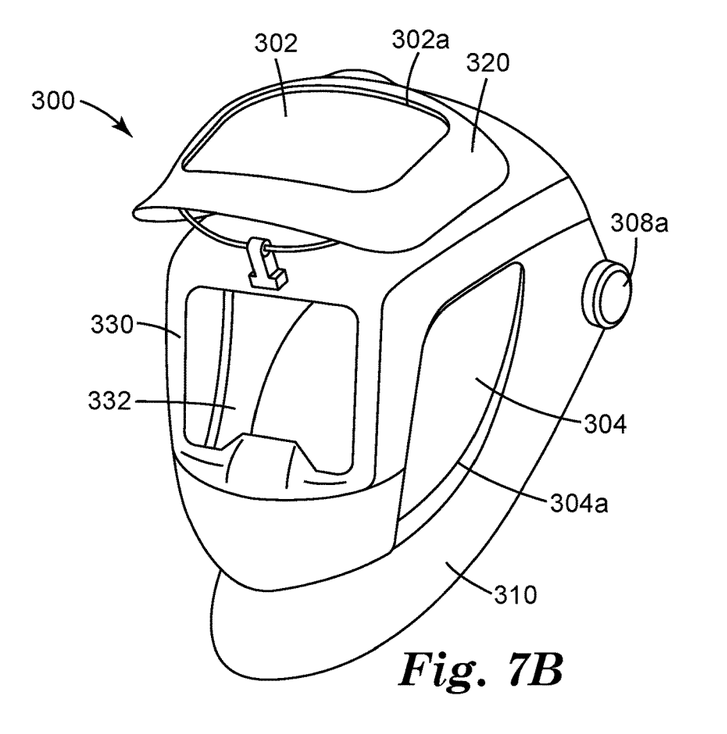

Turning now to FIGS. 7A and 7B, an exemplary welding helmet 300 includes a first face shield 310 and a head harness (not shown). The first face shield 310 is attached to the head harness by two pivot mechanisms 308a and 308b. The pivot mechanisms allow the first face shield 310 to be raised out of view of the welder when not in use, and lowered prior to the welder performing welding operations. The first face shield includes a first aperture 330 and a clear visor 332 arranged in the first aperture 330. The welding helmet 300 further includes a second face shield 320, which is movably attached to the first face shield 310. A main filter 302 is arranged in a second aperture 302a located in the second face shield 320. In a downward position, the second face shield 320 is arranged such that the main filter 302 is in the direct line of vision of the user, so that when a welder is performing welding operations, they can view the point of welding through the main filter 302. In an upward position, the second face shield 320 is arranged such that the main filter 302 is out of the direct line of vision of the user.

Auxiliary filters 304 and 306 are arranged in third and fourth apertures 304a and 306a, respectively, in the face shield 310. Auxiliary filters 304 and 306 are located on either side (left and right) of the main filter 302 and next to it when the second face shield 320 is in the downward position. When the second face shield 320 is in the upward position, auxiliary filters 304 and 306 are located on either side (left and right) of the first aperture 330. Any one or more of the main filter 302 and the auxiliary filters 304 and 306 can comprise one or more electro-optic elements according to the present disclosure.

Figure 8:
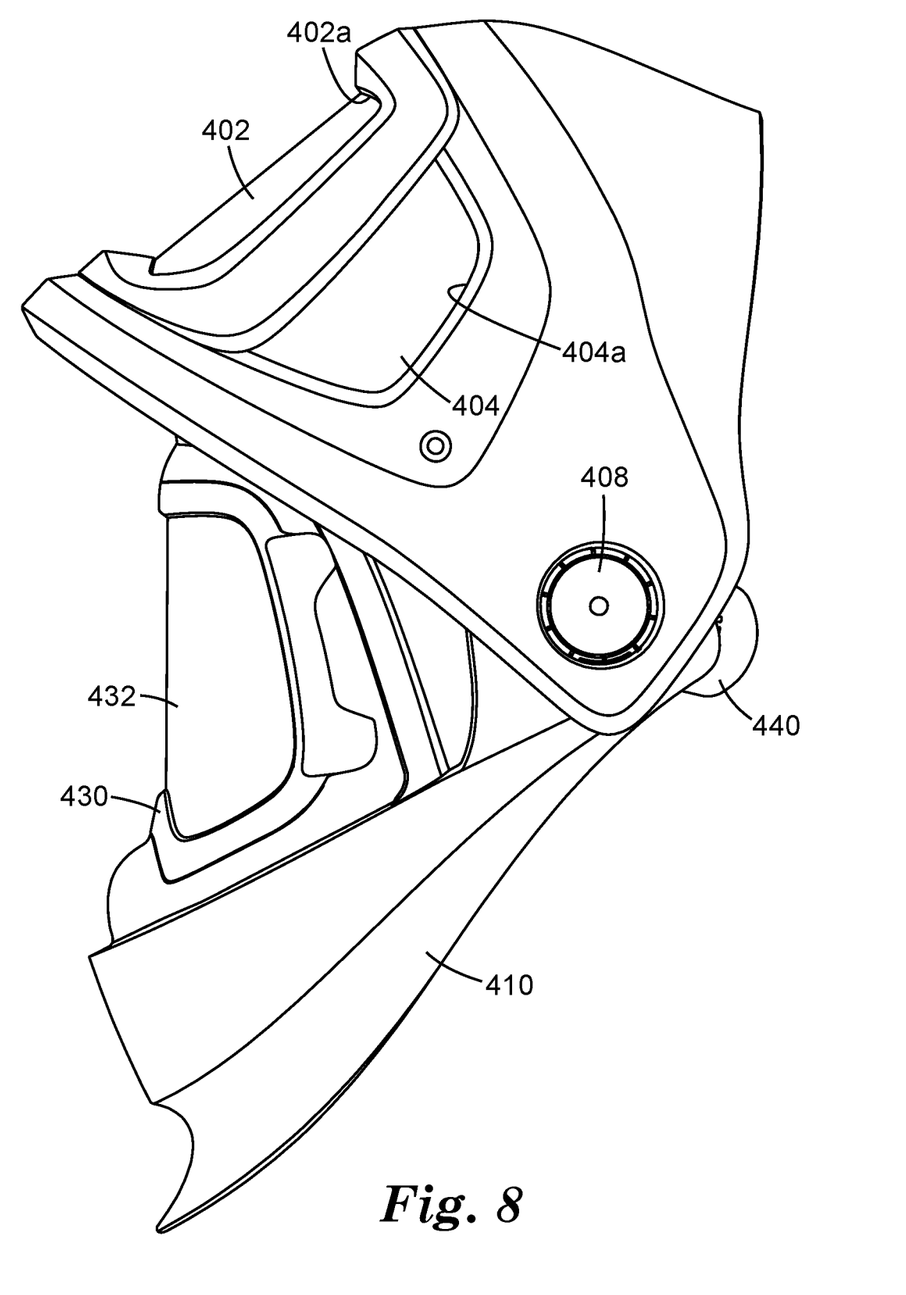
FIG. 8 illustrates a welding helmet according to yet another exemplary embodiment of the present disclosure.

FIG. 8 shows another exemplary welding helmet 400, which includes a first face shield 410 and a head harness 440. The face shield 410 is attached to the head harness 440 by two pivot mechanisms 408 (one not shown). The pivot mechanisms allow the face shield 410 to be raised out of view of the welder when not in use, and lowered prior to the welder performing welding operations. The first face shield 410 includes a first aperture 430 and a clear visor 432 arranged in the first aperture 430. The welding helmet 400 further includes a second face shield 420, which is movably attached to the first face shield 410. In this exemplary embodiment, the second face shield 420 is pivotally attached to the first face shield 410 via the pivot mechanisms 408.

A main filter 402 is arranged in a second aperture 402a located in the second face shield 420. Two auxiliary filters 404 (only one is shown) are arranged in third and fourth apertures 404a (only one is shown) in the second face shield 420. Auxiliary filters 404 are located next to and on either side (left and right) of the main filter 402. In a downward position, the second face shield 420 is arranged such that the main filter 402 is in the direct line of vision of the user while the auxiliary filters 404 are out of the direct line of vision of the user. Thus, when a welder is performing welding operations, he or she can view the point of welding through the main filter 402 and obtain peripheral vision through the auxiliary filters 404. In an upward position, the second face shield 420 is arranged such that the main filter and the auxiliary filters are out of view of the user. As in other exemplary embodiments, any one or more of the main filter 402 and the auxiliary filters 404 can comprise one or more electro-optic elements according to the present disclosure.

Figure 9:
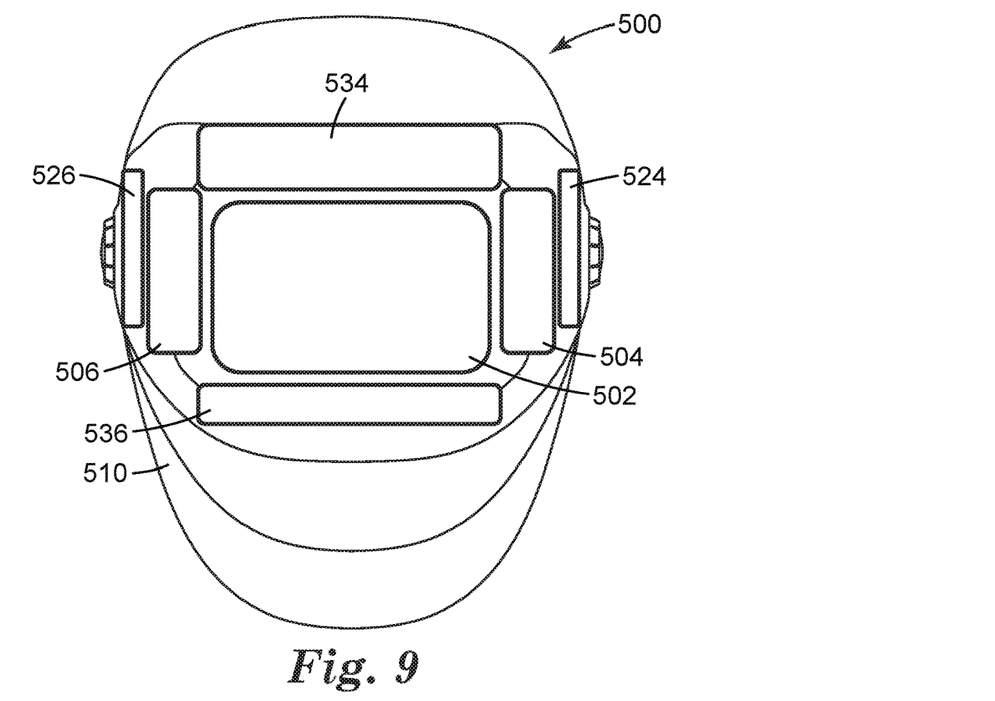
FIG. 9 is a diagrammatic illustration of a welding helmet according a further embodiment of the present disclosure.
Figure 10:
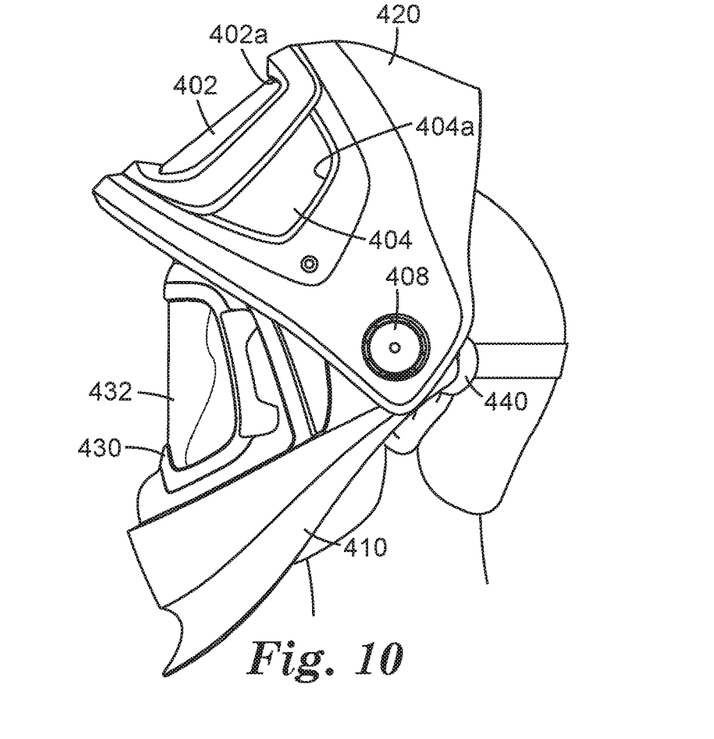
FIG. 10 illustrates a welding helmet according to another embodiment of the present disclosure.

The welding helmets according to the present disclosure have been exemplified so far as having two auxiliary filters that are individual to and separate from the main filter and located next to the main filter, one auxiliary filter on either side of the main filter. FIG. 9 is a diagrammatic illustration of a further welding helmet illustrating yet other embodiments of the present disclosure. A welding helmet 500 may include a face shield 510 including an auxiliary filter 534 located above the main filter 502, either in addition to or instead of the side auxiliary filters 504 and 506 to give the welder better vision of the environment above his or her range of vision through the main filter. For example, this feature may be desirable if the welder is performing welding operations in situations where there is overhead moving machinery. Other arrangements of auxiliary filters, for example, an auxiliary filter 536 located below the main filter 502, that may also be used to improve the welder's peripheral vision and awareness of their surroundings, may be provided.

Alternatively, a matrix of several auxiliary filters may be arranged around the main filter 502. In this situation, the auxiliary filters may be configured to switch at different switching speeds, at different switching thresholds, either independent of each other or in coordination with each other, or any combination of these. The auxiliary filters 504 and 506 may be switchable from shade three (3) to a selectable shade between eight (8) and twelve (12). Depending on the situation that the welder is working in, it may be desirable for the auxiliary filters of a welding helmet to be set to different shades, depending on the welders working location and/or the location of the auxiliary filter on the welding helmet. For example, if the welder is working in a situation with overhead lighting, they may desire an auxiliary filter 534 located above the main filter 502 to have a light shade of shade four (4) to five (5), such that ambient lighting transmitted through the auxiliary filter 534 does not cause unwanted reflections on the main filter 502. Furthermore, where more than one auxiliary filter is located on either side of the main filter 502, it is envisaged that the light shade and dark shades will be chosen to be appropriate for the welding operations. For example, the auxiliary side filters 524 and 526 that are further from the main filter 502 than the auxiliary side filters 504 and 506 may have lighter shades (light, dark or both) than auxiliary filters 504 and 506 that are disposed closer to the main filter 502.

The auxiliary filters may be adapted such that they can be switched by the welder. In this case, one or more auxiliary filters may be provided with a switch in electrical communication with an electronic controller to allow the welder to change the state or shade of the auxiliary filter. It is desired by some welders to have manual control over the state of the filter when the filter switches between its different states. By way of example, where a welder is working in an environment where there are many other welding operations, the welder may desire to have the auxiliary filters in the dark state for a long period of time, such that visible radiation from neighbouring welding operations does not cause distractions regardless of the intensity of the radiation. The welder may then desire to switch the auxiliary filter(s) to a light state when moving from work location to another work location, that is, at times when extended peripheral vision is beneficial.

Furthermore, the auxiliary filter may be configured such that the shade of auxiliary filter may be changed by means of the switch. An electronic controller that is connected to the switch may be configured such that successive presses of the switch cause the auxiliary filter to change through a sequence of different shades. A suitable switch can be a membrane type switch located in the vicinity of the main filter or an auxiliary filter, or in any other suitable location. Preferably, one or more switches may be positioned so that they can be operated by a welder whilst wearing the welding helmet. Various types of switches are within the scope of the present disclosure, such as push button switches and rocker switches.

In welding helmet filter arrangements that include auxiliary filters where switching from one state to another state is infrequent, and triggered by means of a switch, the use of electrochromic technology is particularly advantageous. Where more than one auxiliary filter is included in the filter arrangement of a welding helmet, the switching of the auxiliary filters may be linked to one switch or separate switches. A manual switch may be used in conjunction with an automatic mode. In this case, the switch may be an override switch such that the welder has the choice of either using the auxiliary filter in a manual mode or an automatic mode.

What is claimed is:

1. A welding helmet having a filter arrangement comprising:

a face shield pivotably connected to a head harness fitted internally to the face shield and configured to be secured on a user's head, wherein the face shield is configured to be raised out of view of the user when not in use, and lowered to a working position when the user is to perform a welding operation, wherein the face shield comprises a main central aperture centrally disposed in the face shield at eye level of the user when in the working position, a first side aperture disposed adjacent to and separate from the main central aperture at a first side, and a second side aperture disposed adjacent to and separate from the main central aperture on an opposite second side of the main central aperture;

a main filter, positioned in the first aperture, comprising a first electro-optic element adapted to attenuate transmission of optical radiation incident on the main filter, wherein, in the working position, the main filter is configured to be disposed in front of the user's eyes in a direct line of vision of the user; and a first auxiliary filter separate from the main filter and disposed in the first side aperture, and a second auxiliary filter separate from the main filter and disposed in the second side aperture;

wherein the first auxiliary filter comprises a second electro-optic element adapted to attenuate transmission of optical radiation incident on the first auxiliary filter, and wherein at least the first auxiliary filter is adapted to be switched between a light state and a dark state independently from the main filter.

2. The welding helmet as claimed in claim 1, wherein the second electro-optic element comprises an optically responsive medium disposed between transparent substrates.

3. The welding helmet as claimed in claim 2, wherein the second optically responsive medium comprises a liquid crystal material.

4. The welding helmet as claimed in claim 2, wherein the second optically responsive medium comprises an electrochromic material.

5. The welding helmet as claimed in claim 1, wherein the first electro-optic element of the main filter comprises a liquid crystal material and the at least one auxiliary filter comprises an electrochromic material.

6. The welding helmet as claimed in claim 1, wherein the second electro-optic element is adapted to switch between a first state and at least a second state, wherein the second state attenuates the transmission of optical radiation incident on the first auxiliary filter.

7. The welding helmet as claimed in claim 1, wherein the welding helmet comprises a logic function that is configured to allow the first auxiliary filter to be switched between a light state and a dark state in coordination with the main filter.

8. The welding helmet as claimed in claim 1, wherein the first auxiliary filter comprises an electronic switch that is configured to allow the first auxiliary filter to be switched between a light state and a dark state manually.

9. The welding helmet as claimed in claim 1, wherein the second auxiliary filter comprises a third electro-optic element adapted to attenuate transmission of optical radiation incident on the second auxiliary filter, and wherein the welding helmet comprises electronic controls configured to allow the first and second auxiliary filters to be switched between a light state and a dark state independently from each other.

10. The welding helmet as claimed in claim 1, further comprising a third auxiliary filter disposed above a top side of the main filter.

11. The welding helmet as claimed in claim 1, further comprising a third auxiliary filter disposed below a lower side of the main filter.

12. A welding helmet, comprising:

a head harness configured to be secured on a user's head;

a first face shield configured to cover at least a substantial portion of a user's head and face pivotably connected to the head harness and configured to be placed in front of the user's face when placed in a working position; and a second face shield movably attached to the first face shield, wherein each of the first and second face shields includes a main central aperture centrally disposed in the face shield at eye level of the user when positioned in the working position, a first side aperture disposed adjacent to the main central aperture at a first side, and a second side aperture disposed adjacent to the main central aperture on an opposite second side of the main central aperture;

a main filter positioned in one of the main central aperture of the first face shield and the main central aperture of the second face shield, the main filter comprising a first electro-optic element adapted to attenuate transmission of optical radiation incident on the main filter;

a first auxiliary filter separate from the main filter and disposed in one of the first side aperture of the first face shield and the first side aperture of the second face shield; and a second auxiliary filter separate from the main filter and disposed in one of the second side aperture of the first face shield and the second side aperture of the second face shield, wherein the first auxiliary filter comprises a second electro-optic element adapted to attenuate transmission of optical radiation incident on the first auxiliary filter, and wherein the first auxiliary filter is adapted to be switched between a light state and a dark state independently from the main filter.

13. The welding helmet as claimed in claim 12, wherein the first face shield comprises a pivot mechanism se that is configured to raise and lower the first face shield while the welding helmet is worn.

* * * * *

UNITED STATES PATENT AND TRADEMARK OFFICE
CERTIFICATE OF CORRECTION

PATENT NO. : 10,667,952 B2  
APPLICATION NO. : 13/989123  
DATED : June 2, 2020  
INVENTOR(S) : Kristina Magnusson Page 1 of 1

It is certified that error appears in the above-identified patent and that said Letters Patent is hereby corrected as shown below:

In the Claims

Column 16,
Line 47, after "mechanism" delete "se".

Signed and Sealed this
Twenty-ninth Day of December, 2020

Andrei Iancu
*Director of the United States Patent and Trademark Office*